United States Patent [19]

Kuroda et al.

[11] Patent Number: 5,420,091
[45] Date of Patent: May 30, 1995

[54] METHOD OF PREPARING CATALYST USED FOR PRODUCING METHACRYLIC ACIDS

[75] Inventors: Toru Kuroda, Otake; Motomu Oh-Kita, Tokyo, both of Japan

[73] Assignee: Mitsubishi Rayon Co., Ltd., Tokyo, Japan

[21] Appl. No.: 90,278

[22] Filed: Jul. 13, 1993

[51] Int. Cl.6 .................... B01J 27/18; B01J 27/19
[52] U.S. Cl. ..................... 502/209; 502/211; 502/212; 502/214; 502/308; 502/311; 502/312; 502/321; 502/340; 502/343; 502/344; 502/345; 502/349; 502/353
[58] Field of Search ............... 502/209, 211, 212, 308, 502/311, 312, 349

[56] References Cited

U.S. PATENT DOCUMENTS

| | | | |
|---|---|---|---|
| 4,101,448 | 7/1978 | Shaw et al. | 502/209 |
| 5,104,844 | 4/1992 | Yamamoto et al. | 502/205 |
| 5,173,468 | 12/1992 | Boehning et al. | 502/209 |
| 5,183,793 | 2/1993 | Paparizos et al. | 502/215 |

FOREIGN PATENT DOCUMENTS 0424900  5/1990  European Pat. Off. .

OTHER PUBLICATIONS

Database WPI, Week 9335, Derwent Publications Ltd., London, GB; AN 93-277606 & JP-A-5 192 850 (Mitsubishi) 3 Aug. 1993 (abstract).
Database WPI, Week 8736, Derwent Publications Ltd., London, GB; AN 87-253876 & JP-A-62 175 435 (Mitsubishi) 1 Aug. 1987 (abstract).
Database WPI, Week 8216, Derwent Publications Ltd., London, GB; AN 82-32195E & JP-A-57 045 130 (Mitsubishi) 13 Mar. 1982 (abstract).

*Primary Examiner*—Anthony McFarlane
*Attorney, Agent, or Firm*—Armstrong, Westerman, Hattori, McLeland & Naughton

[57] ABSTRACT

A method of preparing a catalyst used for producing methacrylic acids through gas phase catalytic oxidation of methacrolein with molecular oxygen. The catalyst is represented by the formula:

$$P_a Mo_b V_c Ge_d X_e Y_f Z_g O_h$$

wherein P, Mo, V, Ge and O represent phosphorous, molybdenum, vanadium, germanium and oxygen, respectively; X represents at least one element selected from the group consisting of arsenic, antimony, bismuth, zirconium, tellurium, silver and boron; Y represents at lest one element selected from the group consisting of iron, copper, zinc, chromium, magnesium, tantalum, manganese, barium, gallium, cerium and lanthanum; Z represents at least one element selected from the group consisting of potassium, rubidium, cesium and thallium, and a, b, c, d, e, f, g and h represent the atomic ratios of the respective elements, and when b=12, then a=0.5-3, c=0.01-3, d=0.01-3, e=0-3, f=0-3, g=0.01-3, and h is the number of oxygen atoms necessary for satisfying the above atomic ratios of the respective components. The method includes providing an aqueous mixture containing at least P, Mo, V, Ge, X, Y and Z and removing water from the aqueous mixture, where the improvement comprises providing at least part of the Ge for the aqueous mixture by dissolving germanium dioxide in an aqueous solution of a hydroxide of an element represented by Z in the above formula. The catalyst prepared according to the method is remarkably elevated in activity in the methacrolein oxidation reaction and allows enhancement of the yield of methacrylic acid.

1 Claim, No Drawings

METHOD OF PREPARING CATALYST USED FOR PRODUCING METHACRYLIC ACIDS

BACKGROUND OF THE INVENTION

1. Field of the Invention

The present invention relates to a method of preparing a catalyst used for producing methacrylic acids through gas phase catalytic oxidation of methacrolein with molecular oxygen.

2. Description of the Related Art

Many proposals have been made on the methods and catalysts for producing methacrylic acids through gas phase catalytic oxidation of methacrolein. Especially, ever since discovery of the heteropoly-acid type catalysts, a number of patent applications have been filed regarding the improvements thereof. For example, catalysts containing germanium are disclosed in JP-A-57-45130 and JP-A-62-175435. However, the results of the reactions using the germanium-containing catalysts disclosed in the above patents are still unsatisfactory, and further improvements are required of such catalysts for their industrial use.

SUMMARY OF THE INVENTION

An object of the present invention is to provide a method of preparing a novel catalyst which enables advantageous production of methacrylic acids from methacrolein.

As a result of strenuous studies for improving the conventional catalyst preparation techniques, the present inventors found out a method of preparing a novel catalyst which enables production of methacrylic acids in a significantly higher yield than possible with the catalysts prepared according to the conventional methods.

The present invention consists in a method of preparing a catalyst used for producing methacrylic acids through gas phase catalytic oxidation of methacrolein with molecular oxygen and represented by the formula:

$$P_a Mo_b V_c Ge_d X_e Y_f Z_g O_h$$

wherein P, Mo, V, Ge and O represent phosphorus, molybdenum, vanadium, germanium and oxygen, respectively; X represents at least one element selected from the group consisting of arsenic, antimony, bismuth, zirconium, tellurium, silver and boron; Y represents at least one element selected from the group consisting of iron, copper, zinc, chromium, magnesium, tantalum, manganese, barium, gallium, cerium and lanthanum; Z represents at least one element selected from the group consisting of potassium, rubidium, cesium and thallium; and a, b, c, d, e, f, g and h represent the atomic ratios of the respective components, and when b=12, then a=0.5–3, c=0.01–3, d=0.01–3, e=0–3, f=0–3, g=0.01–3, and h is the number of oxygen atoms required for satisfying the above atomic ratios of the respective components. The method of this invention is characterized by use of germanium dioxide as Ge material, with at least part of said germanium dioxide being dissolved in an aqueous solution of a hydroxide of an element represented by Z in the above formula.

In the present invention, it is imperative that germanium dioxide dissolved in an aqueous solution of a hydroxide of at least one element selected from the group consisting of potassium, rubidium, cesium and thallium is used as Ge source in the catalyst composition. It was found that this feature of the invention, that is, the use of germanium dioxide in the form of solution as Ge material, enables preparation, with good reproducibility, of a catalyst which is increased in activity for the oxidation reaction of methacrolein and in selectivity of methacrylic acids, and therefore allows high-yield production of methacrylic acids. Thus, the present invention is of very high industrial value.

PREFERRED EMBODIMENTS OF THE INVENTION

The method of the present invention is not subject to the specific restrictions in practice thereof except for the definitions of the materials of the Ge and Z components of the catalyst, and the various methods well known in the art such as evaporation-to-dryness method, precipitation method and oxide mixing method can be employed for the preparation of the catalyst as far as no excessively uneven distribution of the components occurs. As the materials of components other than Ge and Z, there can be used nitrates, hydroxides, carbonates, ammonium salts, halides and oxides of the respective elements either singly or in combination. For example, ammonium paramolybdate, molybdenum trioxide and molybdenum chloride can be used as molybdenum material, and ammonium metavanadate, vanadium pentoxide and vanadium chloride can be used as vanadium material.

Germanium dioxide used as Ge material need not be entirely dissolved in an aqueous solution of a hydroxide of an element represented by Z in the above formula; it may be partly dissolved in the aqueous solution to derive the effect of the present invention so long as the atomic ratio of germanium d is 0.01 or more in the above formula. As for the material of the Z component, although it is necessary to use an aqueous solution of a hydroxide of an element represented by Z for dissolving germanium dioxide, part of the component may be constituted by a nitrate, carbonate, halide or oxide of an element represented by Z. The mixture of the elements constituting the respective catalyst components is finally heat treated at 250°–500° C. to produce a catalyst. The shape of the catalyst may be optionally selected. Also, molding of the catalyst may be performed either before or after the heat treatment.

A catalyst according to the present invention may be used without carrier, but it may be supported on an inactive carrier such as silica, alumina, silica-alumina, silicon carbide or the like, or diluted with such material.

In practical use of the catalyst obtained according to the present invention, the concentration of methacrolein in the material gas may vary over a wide range, but usually it is in a range of 1 to 20%, preferably 3 to 10% by volume. Methacrolein used for producing a methacrylic acid by using the catalyst of this invention may contain a small amount of impurities such as water, lower saturated aldehydes, etc. These impurities give substantially no effect to the reaction.

As the oxygen source, it is economical to use air, but if necessary, air enriched with pure oxygen may be used. The oxygen concentration in the material gas is specified by molar ratio to methacrolein, which is 0.3–4, preferably 0.4–2.5. The material gas may be diluted by adding an inert gas such as nitrogen, water vapor, carbon dioxide gas or the like.

The reaction pressure applied in the process of this invention is preferably selected from within a range of normal pressure to several atm.

The reaction temperature may be selected from a range of 230° to 450° C., preferably 250° to 400° C.

The reaction may be carried out either in a fixed bed or in a fluidized bed.

The method of preparation of a catalyst according to the present invention and some examples of the reactions using such a catalyst for producing a methacrylic acid are described in detail below with reference to the examples of the invention and the comparative examples.

In the following Examples and Comparative Examples, the unit "part(s)" is based on weight; the analysis was carried out by means of gas chromatography; and the reaction rate of methacrolein, selectivity of the produced methacrylic acid and its yield are defined as follows.

Reaction rate of methacrolein (%) =

$$\frac{\text{number of moles of reacted methacrolein}}{\text{number of moles of supplied methacrolein}} \times 100$$

Selectivity of methacrylic acid (%) =

$$\frac{\text{number of moles of produced methacrylic acid}}{\text{number of moles of reacted methacrolein}} \times 100$$

Yield of methacrylic acid (%) = reaction rate of methacrolein (%) × selectivity of methacrylic acid (%) × 1/100

EXAMPLE 1

One hundred parts of ammonium paramolybdate and 5.52 parts of ammonium metavanadate were dissolved in 300 parts of pure water. To the resulting solution was added 5.44 parts of 85% phosphoric acid in 10 parts of pure water, and the mixture was heated to 95° C. with stirring. Then a solution formed by dissolving 2.28 parts of copper nitrate in 30 parts of pure water was added. To the resulting mixed solution was further added 0.74 part of germanium dioxide in 13.24 parts of an aqueous 20% potassium hydroxide solution, and the produced solution was heated with stirring and evaporated to dryness. The resultantly obtained solid was dried at 130° C. for 16 hours and pressure molded, followed by a 5-hour heat treatment at 380° C. in air stream to prepare a catalyst. The composition of the obtained catalyst, exclusive of oxygen, was as follows: $P_1Mo_{12}V_1Ge_{0.3}Cu_{0.2}K_1$.

This catalyst was packed in a reaction tube, and a mixed gas consisting of 5% of methacrolein, 10% of oxygen, 30% of water vapor and 55% of nitrogen (% by volume) was passed through the reaction tube at a temperature of 290° C. for a contact time of 3.6 seconds. The resultant product was collected and analyzed by gas chromatography, which showed that the reaction rate of methacrolein was 86.9%, the selectivity of methacrylic acid was 83.3%, and the yield of methacrylic acid was 72.4%.

COMPARATIVE EXAMPLE 1

One hundred parts of ammonium paramolybdate, 5.52 parts of ammonium metavanadate and 4.77 parts of potassium nitrate were dissolved in 300 parts of pure water. To this solution was added 5.44 parts of 85% phosphoric acid in 10 parts of pure water, followed by further addition of 0.74 part of germanium dioxide, and the mixture was heated to 95° C. with stirring. Then a solution formed by dissolving 2.28 parts of copper nitrate in 30 parts of pure water was added, and the mixed solution was heated with stirring and evaporated to dryness. The resulting product was treated in the same way as in Example 1 to prepare a catalyst (comparative catalyst) having a composition consisting of the same elements as the catalyst of Example 1.

When the same reaction as conducted in Example 1 was carried out by using this catalyst, the reaction rate of methacrolein was 85.2%, the selectivity of methacrylic acid was 83.4% and the yield of methacylic acid was 71.1%.

EXAMPLE 2

One hundred parts of molybdenum trioxide, 4.21 parts of vanadium pentoxide and 6.67 parts of 85% phosphoric acid were mixed with 800 parts of pure water. The mixture was heated and stirred under reflux for 3 hours, followed by addition of 0.46 part of copper oxide, 0.92 part of ferrous oxide and 0.72 part of boric acid, and then again heated and stirred under reflux for 2 hours. The resulting slurry was cooled to 50° C., added with 1.21 parts of germanium dioxide in 43.40 parts of an aqueous 20% cesium hydroxide solution, and stirred for 15 minutes. Then a solution formed by dissolving 10 parts of ammonium nitrate in 30 parts of pure water was added, and the mixed solution was heated to 100° C. with stirring and evaporated to dryness. The resultant solid was dried at 120° C. for 16 hours and pressured molded, followed by a 3-hour heat treatment at 380° C. in an air stream to obtain a catalyst. This catalyst had the following composition (exclusive of oxygen): $P_1Mo_{12}V_{0.8}Ge_{0.2}B_{0.2}Cu_{0.1}Fe_{0.2}Cs_1$.

When the reaction of Example 1 was carried out by using this catalyst, the reaction rate of methacrolein was 92.6%, the selectivity of methacrylic acid was 87.6% and the yield of methacrylic acid was 81.1%.

COMPARATIVE EXAMPLE 2

A mixture of 100 parts of molybdenum trioxide, 4.21 parts of vanadium pentoxide, 6.67 parts of 85% phosphoric acid and 800 parts of pure water was heated and stirred under reflux for 3 hours, followed by addition thereto of 0.46 part of copper oxide, 0.92 part of ferrous oxide, 0.72 part of boric acid and 1.21 parts of germanium dioxide and additional 2-hour heating and stirring under reflux. The resulting slurry was cooled to 50° C., mixed with 11.23 parts of cesium bicarbonate in 30 parts of pure water and stirred for 15 minutes. Then 10 parts of ammonium nitrate dissolved in 30 parts of pure water was added, and the mixed solution was heated to 100° C. with stirring to have it evaporated to dryness. The resultant product was treated in the same manner as in Example 2 to prepare a catalyst (comparative catalyst) having a composition consisting of the same elements as the catalyst of Example 2.

When the reaction of Example 1 was carried out by using this catalyst under the same reaction conditions as in Example 2, the reaction rate of methacrolein was 91.0%, the selectivity of methacrylic acid was 87.5% and the yield of methacrylic acid was 79.6%.

EXAMPLE 3

One hundred parts of ammonium paramolybdate and 2.76 parts of ammonium metavanadate were dissolved in 300 parts of pure water, followed by addition of 5.44 parts of 85% phosphoric acid in 10 parts of pure water and heating to 95° C. with stirring. Then 1.23 parts of germanium dioxide in 35.38 parts of an aqueous 20% cesium hydroxide solution was added and the mixed solution was heated with stirring to have it evaporated to dryness. The resultant product was treated in the same manner as in Example 1 to prepare a catalyst. This catalyst had the composition of: $P_1Mo_{12}V_{0.5}Ge_{0.5}Cs_1$.

When the reaction of Example 1 was conducted by using this catalyst, the reaction rate of methacrolein was 86.2%, the selectivity of methacrylic acid was 82.6% and the yield of methacrylic acid was 71.2%.

COMPARATIVE EXAMPLE 3

One hundred parts of ammonium paramolybdate and 2.76 parts of ammonium metavanadate were dissolved in 300 parts of pure water, followed by 5.44 parts of 85% phosphoric acid in 10 parts of pure water and heating to 95° C. with stirring. To the resulting solution were added 1.23 parts of germanium dioxide and then 35.38 parts of an aqueous 20% cesium hydroxide solution, and the mixture was heated with stirring to have it evaporated to dryness. The resultant product was treated in the same manner as in Example 3 to prepare a catalyst (comparative catalyst) having a composition consisting of the same elements as the catalyst of Example 3.

The reaction carried out by using this catalyst under the same reaction conditions as in Example 3 gave the following results: reaction rate of methacrolein = 85.0%; selectivity of methacrylic acid = 82.2%; yield of methacrylic acid = 69.9%.

EXAMPLES 4–13

The catalysts were prepared according to the procedure of Example 1, and the reaction of Example 1 was carried out by using these catalysts at different reaction temperatures, obtaining the results shown in Table 1.

COMPARATIVE EXAMPLES 4–13

The catalysts were prepared according to the procedure of Comparative Example 1, and the reaction of Example 1 was carried out by using these catalysts under the reaction conditions of Examples 4–13, respectively. The obtained results are shown in Table 1.

TABLE 1

| | Catalyst composition | Reaction temperature (°C.) | Reaction rate of methacrolein (%) | Selectivity of methacrylic acid (%) | Yield of methacrylic acid (%) |
|---|---|---|---|---|---|
| Example 4 | $P_1Mo_{12}V_{0.5}Ge_{0.3}Bi_{0.2}Sb_{0.5}Zn_{0.2}La_{0.1}Rb_{0.8}$ | 270 | 90.8 | 87.6 | 79.5 |
| Comp. Example 4 | " | " | 89.4 | 87.5 | 78.2 |
| Example 5 | $P_{1.5}Mo_{12}V_{0.5}Ge_{0.5}Cr_{0.5}Cs_{0.5}Tl_{0.3}$ | 280 | 80.7 | 80.9 | 65.3 |
| Comp. Example 5 | " | " | 78.7 | 81.1 | 63.8 |
| Example 6 | $P_1Mo_{12}V_1Ge_{0.4}Te_{0.2}Cu_{0.1}Fe_{0.2}K_{0.5}Rb_{0.5}$ | 290 | 88.7 | 86.9 | 77.1 |
| Comp. Example 6 | " | " | 87.3 | 86.8 | 75.8 |
| Example 7 | $P_2Mo_{12}V_{0.5}Ge_{0.2}Ta_{0.5}Cs_1$ | 300 | 84.0 | 84.3 | 70.8 |
| Comp. Example 7 | " | " | 82.0 | 84.2 | 69.0 |
| Example 8 | $P_1Mo_{12}V_{0.5}Ge_{0.8}Sb_{0.5}Ce_{0.1}La_{0.1}Mg_{0.2}K_{0.8}$ | 270 | 91.6 | 88.0 | 80.6 |
| Comp. Example 8 | " | " | 90.1 | 87.8 | 79.1 |
| Example 9 | $P_{1.5}Mo_{12}V_{0.8}Ge_{0.4}Ag_{0.1}Cu_{0.2}Ba_{0.1}Mn_{0.05}Cs_1$ | 290 | 88.1 | 87.4 | 77.0 |
| Comp. Example 9 | " | " | 86.0 | 87.4 | 75.2 |
| Example 10 | $P_1Mo_{12}V_{0.6}Ge_{0.2}Cu_{0.2}Ga_{0.2}Ba_{0.1}Tl_{0.8}$ | 270 | 91.3 | 90.6 | 82.2 |
| Comp. Example 10 | " | " | 89.8 | 90.3 | 81.1 |
| Example 11 | $P_{1.5}Mo_{12}V_{0.4}Ge_{0.2}As_{0.2}Zn_{0.2}K_1$ | 290 | 87.3 | 85.3 | 74.5 |
| Comp. Example 11 | " | " | 85.6 | 85.1 | 72.8 |
| Example 12 | $P_1Mo_{12}V_{0.4}Ge_{0.8}Se_{0.3}Cu_{0.1}Ce_{0.1}Rb_1$ | 290 | 85.2 | 85.1 | 72.5 |
| Comp. Example 12 | " | " | 84.3 | 84.0 | 70.8 |
| Example 13 | $P_2Mo_{12}V_{0.5}Ge_{0.5}Zr_{0.2}Cu_{0.2}Cr_{0.1}K_1$ | 290 | 85.1 | 83.7 | 71.2 |
| Comp. Example 13 | " | " | 83.5 | 83.3 | 69.6 |

What is claimed is:

1. In a method of preparing a catalyst used for producing methacrylic acids through gas phase catalytic oxidation of methacrolein with molecular oxygen, the catalyst represented by the formula:

$P_aMo_bV_cGe_dX_eY_fZ_gO_h$ wherein P, Mo, V, Ge and O represent phosphorous, molybdenum, vanadium, germanium and oxygen, respectively; X represents at least one element selected from the group consisting of arsenic, antimony, bismuth, zirconium, tellurium, silver and boron; Y represents at lest one element selected from the group consisting of iron, copper, zinc, chromium, magnesium, tantalum, manganese, barium, gallium, cerium and lanthanum; Z represents at least one element selected from the group consisting of potassium, rubidium, cesium and thallium, and a, b, c, d, e, f, g and h represent the atomic ratios of the respective elements, and when b=12, then a=0.5–3, c=0.01–3, d=0.01–3, e=0–3, f=0–3, g=0.01–3, and h is the number of oxygen atoms necessary for satisfying the above atomic ratios of the respective components, the method comprising providing an aqueous mixture containing at least P, Mo, V, Ge, X, Y and Z and removing water from said aqueous mixture, the improvement comprising providing at least part of the Ge for the aqueous mixture by dissolving germanium dioxide in an aqueous solution of a hydroxide of an element represented by Z in the above formula.

* * * * *